US011154411B2

United States Patent
Einav et al.

(10) Patent No.: US 11,154,411 B2
(45) Date of Patent: Oct. 26, 2021

(54) DEPLOYMENT OF MULTIPLE BILIARY STENTS

(71) Applicant: ENDO GI MEDICAL LTD., Nazareth (IL)

(72) Inventors: Elad Einav, Salit (IL); Ronny Barak, Tel Aviv (IL)

(73) Assignee: ENDO GI MEDICAL LTD., Nazareth (IL)

( * ) Notice: Subject to any disclaimer, the term of this patent is extended or adjusted under 35 U.S.C. 154(b) by 161 days.

(21) Appl. No.: 16/064,843

(22) PCT Filed: Dec. 22, 2016

(86) PCT No.: PCT/IL2016/051368
§ 371 (c)(1),
(2) Date: Jun. 21, 2018

(87) PCT Pub. No.: WO2017/109783
PCT Pub. Date: Jun. 29, 2017

(65) Prior Publication Data
US 2019/0000652 A1    Jan. 3, 2019

(30) Foreign Application Priority Data

Dec. 22, 2015  (GB) .................................. 1522683

(51) Int. Cl.
*A61F 2/95* (2013.01)
*A61F 2/82* (2013.01)
(Continued)

(52) U.S. Cl.
CPC .................. *A61F 2/95* (2013.01); *A61F 2/82* (2013.01); *A61F 2/97* (2013.01);
(Continued)

(58) Field of Classification Search
CPC ........ A61F 2/95; A61F 2/97; A61F 2002/041; A61F 2002/826; A61F 2002/9511;
(Continued)

(56) References Cited

U.S. PATENT DOCUMENTS

| 5,669,924 A | 9/1997 | Shaknovich |
| 6,299,595 B1 | 10/2001 | Dutta et al. |

(Continued)

FOREIGN PATENT DOCUMENTS

EP    1867305 A2    12/2007

OTHER PUBLICATIONS

An Office Action dated May 17, 2016, which issued during the prosecution of UK Patent Application No. 1522683.0.
(Continued)

*Primary Examiner* — Katrina M Stransky
(74) *Attorney, Agent, or Firm* — Momentum IP Group; Marc Van Dyke (57) ABSTRACT

Apparatus (20) is provided for use with a guidewire (12). The apparatus includes a guide tube (22) having a guidewire-engaging portion (122) and a slit (28) extending proximally along a wall of the guide tube, from a distal end (32) of the tube, a proximal end (29) of the slit being located distally to a proximal end (30) of the tube. A first stent (52) surrounds the tube and is advanceable together with the tube into a lumen of a subject, the first stent being slidably advanceable off the distal end of the tube; and a second stent (54), proximal to the first stent, surrounding a proximal portion of the tube, and advanceable off the distal end of the tube into the lumen, and placed alongside the first stent subsequently to advancement of the first stent off the distal end of the tube. Other applications are also described.

15 Claims, 7 Drawing Sheets

(51) Int. Cl.
  *A61F 2/97*    (2013.01)
  *A61F 2/04*    (2013.01)
  *A61M 25/06*   (2006.01)
  *A61M 25/09*   (2006.01)

(52) U.S. Cl.
  CPC ... *A61F 2002/041* (2013.01); *A61F 2002/826* (2013.01); *A61F 2002/9511* (2013.01); *A61F 2230/001* (2013.01); *A61M 25/0662* (2013.01); *A61M 25/09041* (2013.01)

(58) Field of Classification Search
  CPC .............. A61F 2002/9522; A61F 2/954; A61F 2002/9583; A61F 2/966; A61F 2002/9665
  See application file for complete search history.

(56) References Cited

U.S. PATENT DOCUMENTS

| | | |
|---|---|---|
| 7,691,125 B2 | 4/2010 | Ducharme |
| 8,211,087 B2 | 7/2012 | Carter et al. |
| 8,512,389 B2 | 8/2013 | Ayala et al. |
| 8,690,756 B2 | 4/2014 | Deal |
| 8,955,520 B2 | 2/2015 | Devereux et al. |
| 2001/0044622 A1* | 11/2001 | Vardi .................... A61F 2/954 606/1 |
| 2005/0125050 A1 | 6/2005 | Carter et al. |
| 2005/0143770 A1 | 6/2005 | Carter et al. |
| 2005/0222603 A1* | 10/2005 | Andreas .................. A61F 2/958 606/194 |
| 2009/0171427 A1 | 7/2009 | Melsheimer et al. |
| 2010/0121426 A1 | 5/2010 | Howell et al. |
| 2011/0087234 A1* | 4/2011 | Ayala .................... A61B 1/018 606/108 |
| 2013/0030416 A1 | 1/2013 | Fernandes et al. |
| 2015/0011834 A1 | 1/2015 | Ayala et al. |

OTHER PUBLICATIONS

An International Preliminary Report on Patentability dated Jun. 26, 2018, which issued during the prosecution of Applicant's PCT/IL2016/05136.

An International Search Report and a Written Opinion both dated Feb. 10, 2017, which issued during the prosecution of Applicant's PCT/IL2016/051368.

An International Search Report and a Written Opinion both dated Oct. 4, 2019, which issued during the prosecution of Applicant's PCT/IL2019/050713.

* cited by examiner

DEPLOYMENT OF MULTIPLE BILIARY STENTS

CROSS-REFERENCES TO RELATED APPLICATIONS

The present application is the US national phase of PCT Application No. PCT/IL2016/051368 to Einav et al., filed on Dec. 22, 2016, published as WO 2017/109783 to Einav et al., and claims the priority of U.K. Patent Application No. 1522683.0 to Einav, entitled "Deployment of Multiple Biliary Stents," filed Dec. 22, 2015, the two above-identified applications are incorporated herein by reference.

FIELD OF THE INVENTION

Embodiments of the present invention relate generally to medical devices and more particularly to methods and apparatus for deploying multiple stents in a lumen of a subject.

BACKGROUND

Stents are typically deployed within a lumen of a body of a subject for various reasons. In some cases, a stent is deployed within a lumen in order to widen a narrowed section of the lumen. For example, insertion of a biliary stent into a bile duct is used to treat obstructions and strictures that occur in the bile duct. There are several conditions, malignant or benign, that can cause strictures of the bile duct. Pancreatic cancer is a common malignant cause of strictures of the bile duct. Noncancerous causes of bile duct stricture may include injury to the bile duct that occurs during surgery for gallbladder removal, and pancreatitis.

A biliary stent is typically a tube-like structure that is used to support a narrowed part of the bile duct and inhibit the reformation of the stricture.

SUMMARY OF THE INVENTION

In accordance with some applications of the present invention, apparatus and method are provided for deployment of more than one stent (e.g., two stents) within a lumen of a subject. For example, two or more stents are deployed within a common bile duct of a subject in order to treat biliary strictures and obstructions. Typically, the two or more stents, e.g., two, three or four stents, are deployed alongside each other within the common bile duct to facilitate relieving of the biliary stricture. Typically, a guide tube is used to deploy the more than one stents (e.g., a first and a second stent) in the lumen of the subject. The guide tube has a proximal end at a proximal portion thereof, and a distal end at a distal portion thereof. In this context, in the specification and in the claims, "proximal" means closer to the orifice through which the guide tube or stent is originally placed into the body, and "distal" means further from this orifice. The guide tube is typically shaped to define a guidewire-engaging portion, e.g., a hole, through a wall of the guide tube, the hole being located at the distal portion of the guide tube. Additionally, the guide tube is shaped to define a slit extending proximally along the wall of the guide tube, from the distal end of the guide tube. A proximal end of the slit is typically located distally to the proximal end of the guide tube. Additionally, a proximal end of the slit is typically located proximally to the hole.

During delivery into the lumen of the subject, the first stent surrounds the guide tube and is advanced together with the guide tube into the lumen of the subject. Typically, the first stent is slidable along the guide tube such that the proximal end of the first stent is disposed distally to the proximal end of the slit of the guide tube while the distal end of the first stent is disposed proximally to the hole of the guide tube. When positioned at a desired site within the lumen of the subject, the first stent is slidably advanced off of the distal end of the guide tube and deployed within the lumen.

The second stent is disposed proximal to the first stent, and surrounds a proximal portion of the guide tube. The second stent is shaped and sized to be advanced over the guide tube and off of the distal end of the guide tube into the lumen of the subject. The second stent is placed alongside the first stent subsequently to advancement of the first stent off of the distal end of the guide tube.

In accordance with some applications of the present invention, the first and second stents are delivered to the lumen of the subject without removing the guide tube from the body of the subject following deployment of the first stent in order to mount the second stent. As provided by some applications of the present invention, the first and second stents are mounted onto the guide tube and advanced into the subject's body to be deployed subsequently within the lumen of the subject, as described above.

There is therefore provided in accordance with some applications of the present invention, apparatus for use with a guidewire, the apparatus including:

a guide tube shaped to define (a) a guidewire-engaging portion at a distal portion of the guide tube, and (b) a slit extending proximally along a wall of the guide tube, from a distal end of the guide tube, a proximal end of the slit being located distally to a proximal end of the guide tube;

a first stent surrounding the guide tube so as to be advanceable together with the guide tube into a lumen of a subject, the first stent being slidable along the guide tube such that a proximal end of the first stent is disposable distally to the proximal end of the slit while a distal end of the first stent is disposed proximally to the guidewire-engaging portion, the first stent being slidably advanceable off the distal end of the guide tube; and a second stent, proximal to the first stent, surrounding a proximal portion of the guide tube, and shaped and sized to be advanceable along the guide tube and off the distal end of the guide tube into the lumen, and placed alongside the first stent subsequently to advancement of the first stent off the distal end of the guide tube, the guide tube is shaped such that when the guidewire is disposed (i) at least in part in a lumen of the guide tube, (ii) passing through a distal-end opening of the guide tube, (iii) passing through the guidewire-engaging portion of the guide tube, and (iv) passing through the proximal end of the slit:

the first stent is (i) constrained from distal motion past the guidewire-engaging portion, and (ii) constrained from proximal motion past the proximal end of the slit.

For some applications, the guidewire-engaging portion is shaped as a hole through the wall of the guide tube.

For some applications, the hole is disposed at an angular offset of 90-180 degrees from the slit, with respect to a central longitudinal axis of the guide tube.

For some applications, the hole is disposed at an angular offset of 180 degrees from the slit, with respect to the central longitudinal axis of the guide tube.

For some applications, a distance between a center of the hole and the distal end of the guide tube is at least 5 mm.

For some applications, a distance between a center of the hole and the distal end of the guide tube is less than 200 mm.

For some applications, the hole is shaped to define an elliptical hole having a major axis oriented in parallel with a longitudinal axis of the guide tube.

For some applications, the guide tube is shaped such that when the guidewire is disposed (i) at least in part in the lumen of the guide tube, (ii) passing through the distal-end opening of the guide tube, (iii) passing through the guidewire-engaging portion of the guide tube, and (iv) passing through the proximal end of the slit:

the second stent is constrained from distal motion past the proximal end of the slit.

For some applications, the apparatus further includes the guidewire.

For some applications, the first stent is slidably advanceable off the distal end of the guide tube when the guidewire is not passing through the guidewire-engaging portion of the guide tube.

For some applications, the lumen of the subject includes a common bile duct of the subject, and the apparatus is advanceable into the common bile duct.

For some applications, the first stent has a length of 5-15 cm.

For some applications, the slit has a length that is greater than the length of the first stent.

For some applications, the second stent has a length of 5-15 cm.

For some applications, the slit has a length of 5-15 cm.

For some applications, the slit has a length that is: (a) greater than a length of the first stent, and (b) less than a sum of the length of the first stent and a length of the second stent.

For some applications, the slit defines two slit edges that are parallel to a central longitudinal axis of the guide tube, a distance between a first one of the slit edges and a second one of the slit edges being 0.45-0.9 mm For some applications, the slit defines two slit edges that are parallel to a central longitudinal axis of the guide tube, such that, were the guide tube to be viewed from the distal end of the guide tube, an angle of 10-80 degrees is formed that is defined by:

(a) a first line extending from the central longitudinal axis to a first one of the slit edges, and (b) a second line extending from the central longitudinal axis to a second one of the slit edges.

For some applications, the angle is 20-70 degrees.

For some applications, a distal end of the second stent is disposed proximally to the proximal end of the slit.

For some applications, a distal end of the second stent is disposed distally to the proximal end of the slit.

For some applications, the first stent includes a self-expandable stent.

For some applications, the second stent includes a self-expandable stent.

For some applications, the apparatus further includes a third stent, proximal to the second stent, surrounding a proximal portion of the guide tube, and shaped and sized to be advanceable along the guide tube and off of the distal end of the guide tube into the lumen, and placed alongside the first and second stents subsequently to advancement of the first and second stents off of the distal end of the guide tube.

For some applications, the apparatus further includes a fourth stent, proximal to the third stent, surrounding a proximal portion of the guide tube, and shaped and sized to be advanceable along the guide tube and off the distal end of the guide tube into the lumen, and placed alongside the first, second and third stents subsequently to advancement of the first, second, and third stents off of the distal end of the guide tube.

For some applications, the slit is shaped to define the guidewire-engaging portion and a distance between a first one of the slit edges and a second one of the slit edges at the guidewire-engaging portion is 0.09-0.45 mm.

For some applications, the guidewire-engaging portion has a length of 0.45-4.5 mm.

There is further provided in accordance with some applications of the present invention apparatus including:

a guide tube shaped to define (a) a hole through a wall of the guide tube at a distal portion of the guide tube, and (b) a slit extending proximally along the wall of the guide tube, from a distal end of the guide tube, a proximal end of the slit being located distally to a proximal end of the guide tube;

a first stent surrounding the guide tube so as to be advanceable together with the guide tube into a lumen of a subject, the first stent being slidable along the guide tube such that a proximal end of the first stent is disposable distally to the proximal end of the slit while a distal end of the first stent is disposed proximally to the hole, the first stent being slidably advanceable off of the distal end of the guide tube; and a second stent, proximal to the first stent, surrounding a proximal portion of the guide tube, and shaped and sized to be advanceable along the guide tube and off of the distal end of the guide tube into the lumen, and placed alongside the first stent subsequently to advancement of the first stent off of the distal end of the guide tube.

For some applications, the apparatus further includes a guidewire configured to (i) enter a lumen of the guide tube from a distal-end opening of the guide tube, (ii) pass out of the lumen of the guide tube through the hole of the guide tube, and (iii) pass into the lumen of the guide tube through the proximal end of the slit, and the first stent is (i) constrained from distal motion past the hole when the guidewire is disposed within the hole, and (ii) constrained from proximal motion past the proximal end of the slit when the guidewire is disposed within the slit.

For some applications, the first stent is slidably advanceable off the distal end of the guide tube when the guidewire is not disposed within the hole.

For some applications, the lumen of the subject includes a common bile duct of the subject, and the apparatus is advanceable into the common bile duct.

For some applications, the hole is disposed at an angular offset of 90-180 degrees from the slit, with respect to a central longitudinal axis of the guide tube.

For some applications, the hole is disposed at an angular offset of 180 degrees from the slit, with respect to the central longitudinal axis of the guide tube.

For some applications, a distance between a center of the hole and the distal end of the guide tube is at least 5 mm.

For some applications, a distance between a center of the hole and the distal end of the guide tube is less than 200 mm.

For some applications, the first stent has a length of 5-15 cm.

For some applications, the slit has a length that is greater than the length of the first stent.

For some applications, the second stent has a length of 5-15 cm.

For some applications, the slit has a length of 5-15 cm.

For some applications, the slit has a length that is: (a) greater than a length of the first stent, and (b) less than a sum of the length of the first stent and a length of the second stent.

For some applications, the hole is shaped to define an elliptical hole.

For some applications, the major axis of the elliptical hole is oriented in parallel with a longitudinal axis of the guide tube.

For some applications, the elliptical hole has a major axis having a length of 5-10 mm and a minor axis having a length of 0.5-1.0 mm.

For some applications, the major axis is 1.5-4 times longer than the minor axis.

For some applications, the slit defines two slit edges that are parallel to a central longitudinal axis of the guide tube, a distance between a first one of the slit edges and a second one of the slit edges being 0.45-0.9 mm.

For some applications, the slit defines two slit edges that are parallel to a central longitudinal axis of the guide tube, such that, were the guide tube to be viewed from the distal end of the guide tube, an angle of 10-80 degrees is formed that is defined by:
(a) a first line extending from the central longitudinal axis to a first one of the slit edges, and
(b) a second line extending from the central longitudinal axis to a second one of the slit edges.

For some applications, the angle is 20-70 degrees.

For some applications, a distal end of the second stent is disposed proximally to the proximal end of the slit.

For some applications, a distal end of the second stent is disposed distally to the proximal end of the slit.

For some applications, the first stent includes a self-expandable stent.

For some applications, the second stent includes a self-expandable stent.

For some applications, the apparatus further includes a third stent, proximal to the second stent, surrounding a proximal portion of the guide tube, and shaped and sized to be advanceable along the guide tube and off of the distal end of the guide tube into the lumen, and placed alongside the first and second stents subsequently to advancement of the first and second stents off of the distal end of the guide tube.

For some applications, the apparatus further includes a fourth stent, proximal to the third stent, surrounding a proximal portion of the guide tube, and shaped and sized to be advanceable along the guide tube and off of the distal end of the guide tube into the lumen, and placed alongside the first, second and third stents subsequently to advancement of the first, second, and third stents off of the distal end of the guide tube.

There is further provided in accordance with some applications of the present invention, apparatus, including:
a guide tube shaped to define (a) a hole through a wall of the guide tube at a distal portion of the guide tube, and (b) a slit extending proximally along the wall of the guide tube, from a distal end of the guide tube, a proximal end of the slit being located distally to a proximal end of the guide tube;
a first stent surrounding the guide tube, the first stent being slidable along the guide tube such that a proximal end of the first stent is disposable distally to the proximal end of the slit while a distal end of the first stent is disposed proximally to the hole, the first stent being slidably advanceable off of the distal end of the guide tube; and
a second stent, proximal to the first stent, surrounding the proximal portion of the guide tube, and shaped and sized to be advanceable over the guide tube.

For some applications, the apparatus further includes a guidewire configured to (i) enter a lumen of the guide tube from a distal-end opening of the guide tube, (ii) pass out of the lumen of the guide tube through the hole of the guide tube, and (iii) pass into the lumen of the guide tube through the proximal end of the slit, and the first stent is (i) constrained from distal motion past the hole when the guidewire is disposed within the hole, and (ii) constrained from proximal motion past the proximal end of the slit when the guidewire is disposed within the slit.

For some applications, the first stent is slidably advanceable off the distal end of the guide tube when the guidewire is not disposed within the hole.

For some applications, the hole is disposed at an angular offset of 90-180 degrees from the slit, with respect to a central longitudinal axis of the guide tube.

For some applications, the hole is disposed at an angular offset of 180 degrees from the slit, with respect to the central longitudinal axis of the guide tube.

For some applications, a distance between a center of the hole and the distal end of the guide tube is at least 5 mm.

For some applications, a distance between a center of the hole and the distal end of the guide tube is less than 200 mm.

For some applications, the first stent has a length of 5-15 cm.

For some applications, the slit has a length that is greater than the length of the first stent.

For some applications, the second stent has a length of 5-15 cm.

For some applications, the slit has a length of 5-15 cm.

For some applications, the slit has a length that is: (a) greater than a length of the first stent, and (b) less than a sum of the length of the first stent and a length of the second stent.

For some applications, the hole is shaped to define an elliptical hole.

For some applications, the major axis of the elliptical hole is oriented in parallel with a longitudinal axis of the guide tube.

For some applications, the elliptical hole has a major axis having a length of 5-10 mm and a minor axis having a length of 0.5-1.0 mm.

For some applications, the major axis is 1.5-4 times longer than the minor axis.

For some applications, the slit defines two slit edges that are parallel to a central longitudinal axis of the guide tube, a distance between a first one of the slit edges and a second one of the slit edges being 0.45-0.9 mm.

For some applications, the slit defines two slit edges that are parallel to a central longitudinal axis of the guide tube, such that, were the guide tube to be viewed from the distal end of the guide tube, an angle of 10-80 degrees is formed that is defined by:
(a) a first line extending from the central longitudinal axis to a first one of the slit edges, and
(b) a second line extending from the central longitudinal axis to a second one of the slit edges.

For some applications, the angle is 20-70 degrees.

For some applications, a distal end of the second stent is disposed proximally to the proximal end of the slit.

For some applications, a distal end of the second stent is disposed distally to the proximal end of the slit.

For some applications, the first stent includes a self-expandable stent.

For some applications, the second stent includes a self-expandable stent.

There is further provided in accordance with some applications of the present invention, a method including:
providing apparatus including:
a guide tube shaped to define (a) a hole through a wall of the guide tube at a distal portion of the guide tube, and (b) a slit extending proximally along the wall of the guide tube, from a distal end of the guide tube, a proximal end of the slit being located distally to a proximal end of the guide tube, a first stent surrounding the distal portion of the guide tube, and a second stent, proximal to the first stent, surrounding a proximal portion of the guide tube;

threading a guidewire through the guide tube, such that, following the threading:

(a) the guidewire enters a lumen of the guide tube from a distal-end opening of the guide tube, (b) the guidewire passes out of the lumen of the guide tube through the hole of the guide tube, (c) the first stent is constrained from distal motion past the hole of the guide tube, due to the guidewire being disposed within the hole, (d) the guidewire passes into the lumen of the guide tube through the slit, and (e) the first stent is constrained from proximal motion past the proximal end of the slit, due to the guidewire being disposed within the slit.

For some applications the method further includes:

advancing the apparatus to a desired location in a lumen of a subject while the guidewire is threaded through the guide tube and an outer surface of the first stent is disposed against the guidewire;

subsequently to the advancing of the apparatus, removing the guidewire from the hole;

subsequently to the removing, advancing the first stent along the guide tube and off of the distal end of the guide tube into the lumen until the first stent is deployed in the desired location in the lumen of the subject;

subsequently to advancing the first stent off of the distal end of the guide tube, advancing the second stent along the guide tube and over the guidewire in the lumen of the subject; and subsequently to advancing the first stent, advancing the second stent off of the distal end of the guide tube, and placing the second stent alongside the first stent.

There is further provided in accordance with some applications of the present invention, a method including:

providing apparatus including:

a guide tube shaped to define (a) a guidewire-engaging portion at a distal portion of the guide tube, and (b) a slit extending proximally along a wall of the guide tube, from a distal end of the guide tube, a proximal end of the slit being located distally to a proximal end of the guide tube, a first stent surrounding the distal portion of the guide tube, and a second stent, proximal to the first stent, surrounding a proximal portion of the guide tube; threading a guidewire through the guide tube, such that, following the threading:

(a) the guidewire enters a lumen of the guide tube from a distal-end opening of the guide tube, (b) the guidewire passes through the guidewire-engaging portion of the guide tube, (c) the first stent is constrained from distal motion past the guidewire-engaging portion of the guide tube, due to the guidewire passing through the guidewire-engaging portion, (d) the guidewire passes into the lumen of the guide tube through the slit, and (e) the first stent is constrained from proximal motion past the proximal end of the slit, due to the guidewire being disposed within the slit.

For some applications the method further includes:

advancing the apparatus to a desired location in a lumen of a subject while the guidewire is threaded through the guide tube and an outer surface of the first stent is disposed against the guidewire;

subsequently to the advancing of the apparatus, removing the guidewire from the guidewire-engaging portion;

subsequently to the removing, advancing the first stent along the guide tube and off of the distal end of the guide tube into the lumen until the first stent is deployed in the desired location in the lumen of the subject;

subsequently to advancing the first stent off of the distal end of the guide tube, advancing the second stent along the guide tube and over the guidewire in the lumen of the subject; and subsequently to advancing the first stent, advancing the second stent off of the distal end of the guide tube, and placing the second stent alongside the first stent.

There is further provided in accordance with some applications of the present invention, a method including:

providing (i) a first stent and (ii) a second stent proximal to the first stent;

advancing the first stent against a guidewire into a lumen of a subject;

deploying the first stent in the lumen of the subject;

while maintaining the guidewire in the lumen of the subject subsequently to deployment of the first stent, advancing the second stent over the guidewire into the lumen of the subject; and deploying the second stent in the lumen alongside the first stent.

There is further provided in accordance with some applications of the present invention, apparatus including:

a first stent configured to be advanced into a lumen of a subject against the guidewire; and a second stent proximal to the first stent, and configured to be advanced into the lumen of the subject over the guidewire.

For some applications, the apparatus further includes the guidewire.

For some applications, an outer surface of the first stent is disposed against the guidewire and the second stent surrounds the guidewire.

For some applications, the apparatus further includes a third stent, proximal to the second stent and configured to be advanced into the lumen of the subject over the guidewire.

For some applications, the apparatus further includes a fourth stent, proximal to the third stent and configured to be advanced into the lumen of the subject over the guidewire.

The present invention will be more fully understood from the following detailed description of applications thereof, taken together with the drawings, in which:

DETAILED DESCRIPTION OF EMBODIMENTS

The present detailed description begins with a description of a guide tube 22 which is used to deploy multiple stents in a lumen of the subject, in accordance with some applications of the present invention.

Figure 1:
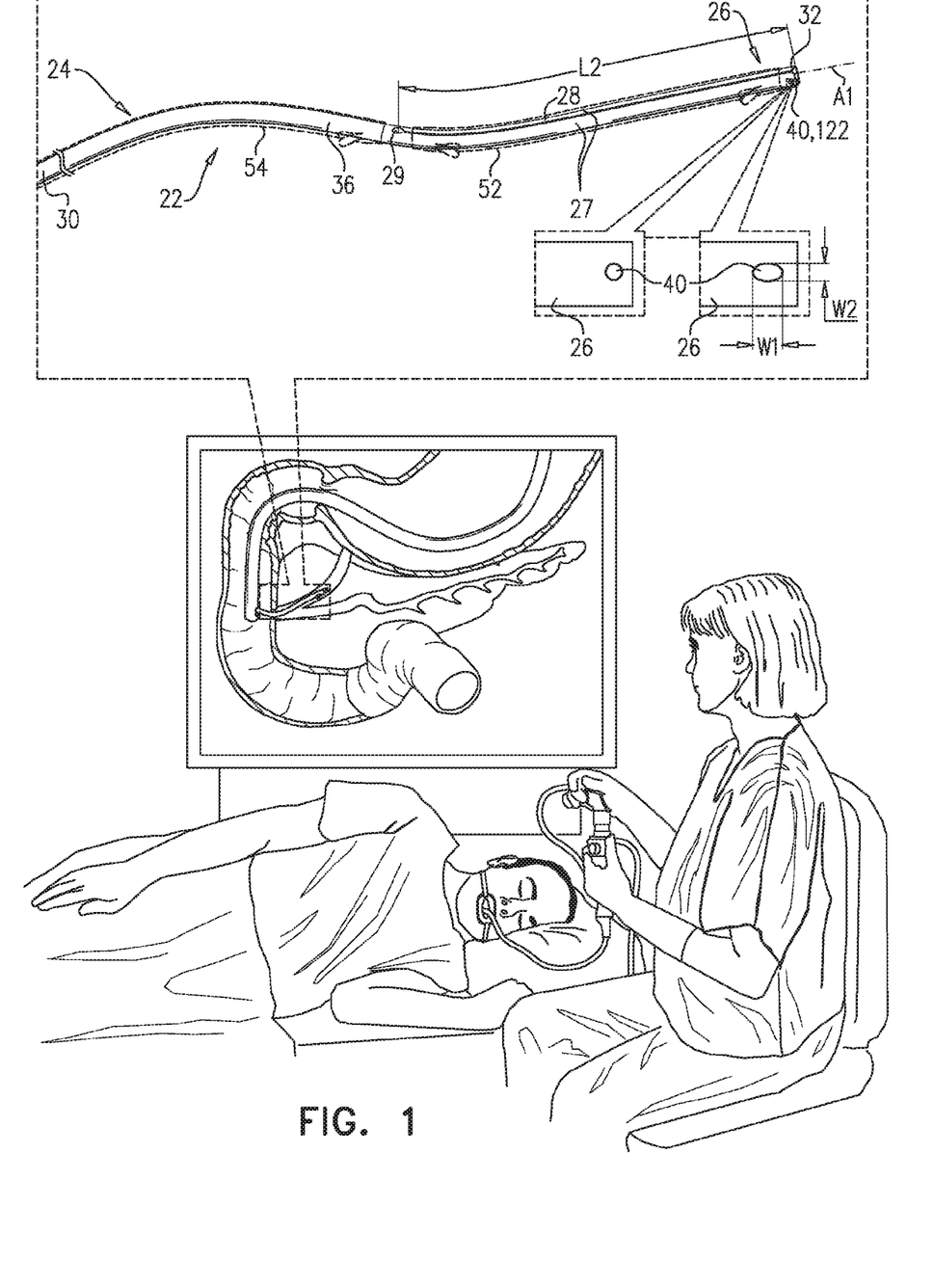
FIG. 1 is a schematic illustration of a guide tube for deployment of a first and second stent in a lumen of a subject, in accordance with some applications of the present invention.
Figure 2:
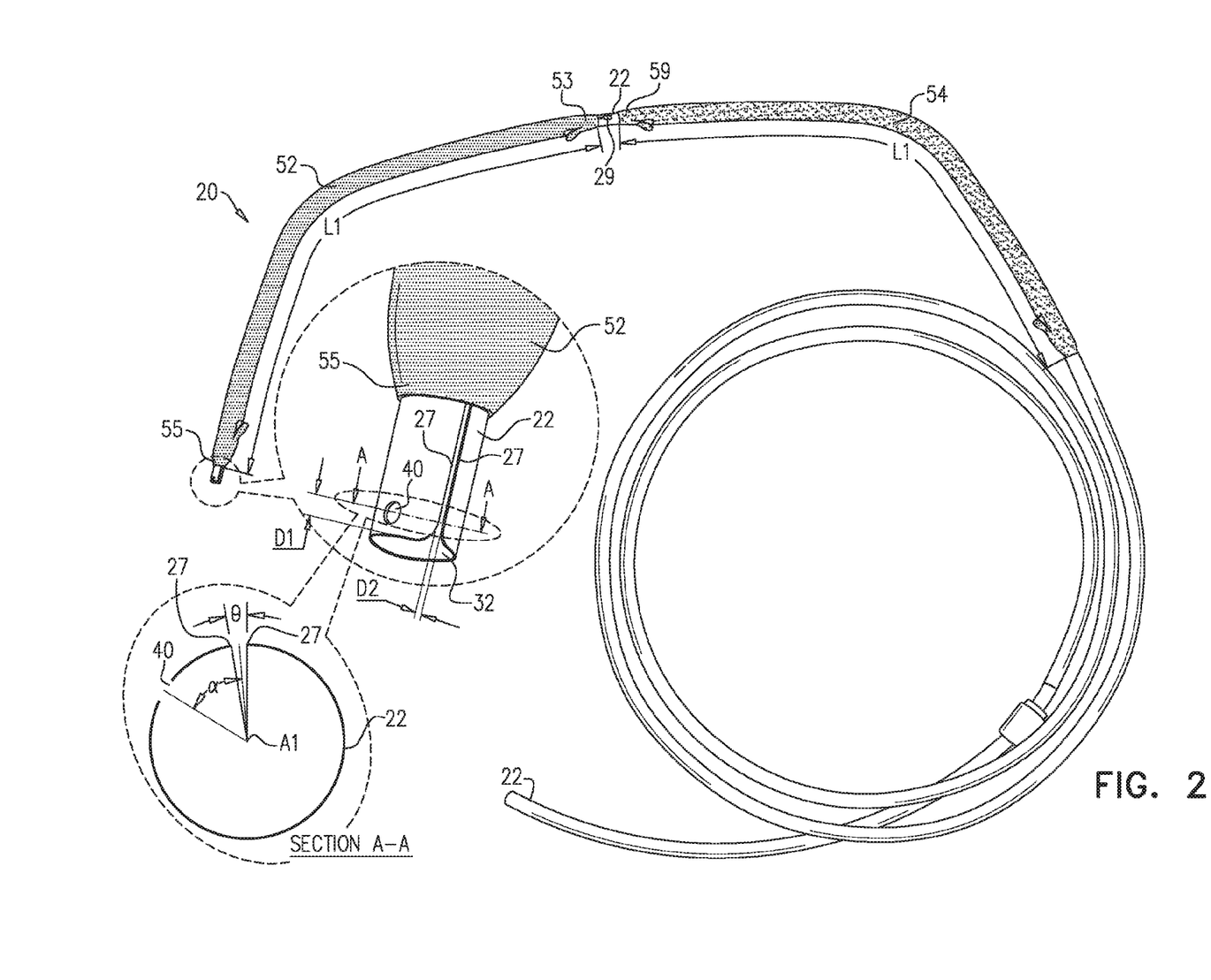
FIG. 2 is a schematic illustration of apparatus for delivery and deployment of a first and second stent in a lumen of a subject, in accordance with some applications of the present invention.

Reference is made to FIGS. 1 and 2.

FIG. 1 is a schematic illustration of guide tube 22, in accordance with some applications of the present invention. As shown, guide tube 22 is shape to define a proximal end 30 at a proximal portion 24 of guide tube 22, and a distal end 32 at a distal portion 26 of guide tube 22.

Guide tube 22 is additionally shaped to define a guidewire-engaging portion 122, shown as a hole 40 through a wall 36 of guide tube 22 at distal portion 26 of the guide tube. Guide tube 22 is further additionally shaped to define a slit 28 extending proximally along wall 36 of guide tube 22, from distal end 32 of the guide tube. A proximal end 29 of slit 28 is located distally to proximal end 30 of guide tube 22. Additionally, proximal end 29 of slit 28 is located proximally to hole 40.

Typically, hole 40 is disposed at an angular offset alpha of 90-180 degrees, e.g., 180 degrees, from slit 28, with respect to a central longitudinal axis A1 of the guide tube. Alternatively, a smaller angle alpha is used (e.g., an angle alpha of approximately 60 degrees is shown in FIG. 2). As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.) The central longitudinal axis of a curved elongate structure is curved, rather than straight.

Typically, a distance D1 between a center of hole 40 and distal end 32 of guide tube 22 is at least 5 mm and/or less than 200 mm e.g., between 5 and 200 mm.

For some applications, hole 40 is shaped to define an elliptical hole having a major axis W1 which is typically oriented in parallel with longitudinal axis A1 of guide tube 22. The major axis is typically 1.5-4 times longer than a minor axis W2 of hole 40. For example, hole 40 has major axis W1 having a length of 5-10 mm and minor axis W2 having a length of 0.5-1.0 mm Slit 28 defines two slit edges 27 that are parallel to central longitudinal axis A1 of guide tube 22, typically a distance D2 between a first one of the slit edges and a second one of the slit edges being 0.45-0.9 mm. For some applications, when guide tube 22 is viewed from distal end 32 of guide tube 22, an angle theta of 10-80 degrees, e.g., 20-70 degrees, is formed that is defined by: (a) a first line extending from the central longitudinal axis to a first one of the slit edges, and (b) a second line extending from the central longitudinal axis to a second one of the slit edges.

Reference is still made to FIGS. 1 and 2. FIG. 2 is a schematic illustration of apparatus 20 for delivery and deployment of a first stent 52 and a second stent 54 in a lumen of a subject, in accordance with some applications of the present invention.

For some applications, apparatus 20 comprises guide tube 22 (as described hereinabove with reference to FIG. 1), and first and second stents 52 and 54 respectively. As shown, first and second stents 52 and 54 surround guide tube 22, second stent 54 being disposed proximally to first stent 52 and surrounding proximal portion 24 of guide tube 22. First stent 52 is typically disposed over guide tube 22 such that a proximal end 53 of first stent 52 is disposed distally to proximal end 29 of slit 28 of guide tube 22 while a distal end 55 of first stent 52 is disposed proximally to hole 40.

For some applications, a distal end 59 of second stent 54 is disposed proximally to proximal end 29 of slit 28. For other applications, distal end 59 of second stent 54 is disposed distally to proximal end 29 of slit 28.

First stent 52 is slidably advanceable off of distal end 32 of guide tube 22. Additionally, second stent 54, is also shaped and sized to be advanceable over guide tube 22, typically subsequently to advancement of first stent 52 off of distal end 32 of guide tube 22.

For some applications, first and second stents 52 and 54 each have a length L1 of 5-15 cm, and slit 28 also has a length L2 of 5-15 cm. Typically, slit 28 has a length that is greater than the length of first stent 52. For some applications, slit 28 has a length that is: (a) greater than a length of first stent 52, and (b) less than a sum of the length of first stent 52 and a length of second stent 54.

Apparatus 20 is typically advanced into a lumen of the subject, and guide tube 22 facilitates placement of first and second stents 52 and 54 within the lumen of the subject.

Reference is now made to FIGS. 3A-H, which depict a general overview of a method for use of apparatus 20 for deploying first and second stents 52 and 54 in a lumen of a subject, in accordance with some applications of the present invention. Typically, stents 52 and 54 are deployed in the lumen of the subject, e.g., a common bile duct of the subject, in order to manage strictures of the lumen. In accordance with some applications of the present invention, apparatus 20 is configured such that first stent 52 is advanced into the lumen of the subject against a guidewire, and second stent 54 is advanced into the lumen over the guidewire (i.e., surrounding the guidewire).

Figure 3A:
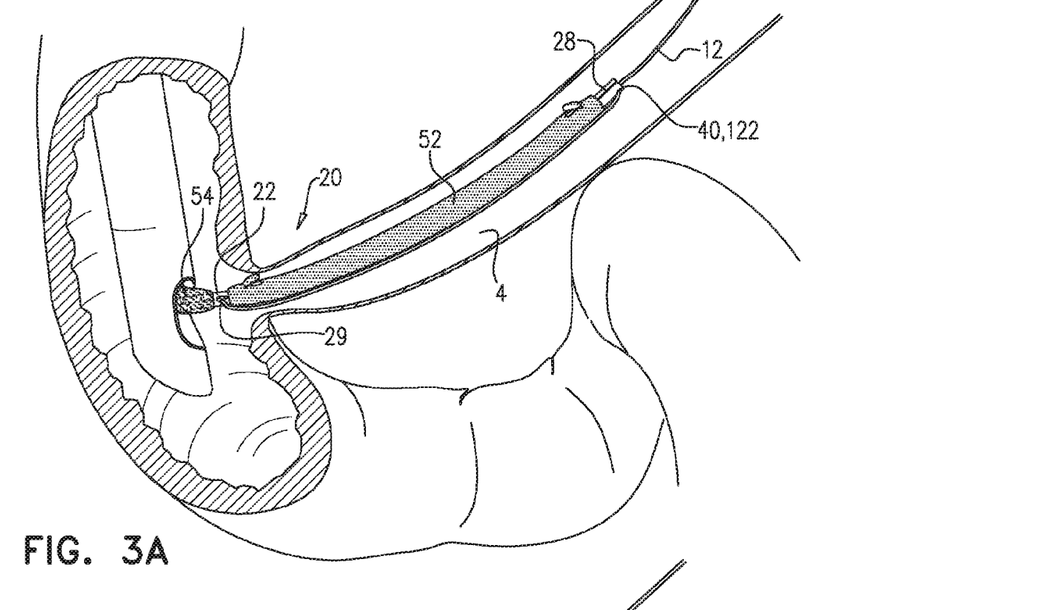
FIGS. 3A-H are schematic illustrations depicting a general overview of a method for deploying first and second stents in a lumen of a subject, in accordance with some applications of the present invention.

Reference is made to FIG. 3A. In accordance with some applications of the present invention, apparatus 20 (comprising guide tube 22 and first and second stents 52 and 54, as described hereinabove with reference to FIG. 2) is used in combination with a guidewire 12 to deploy stents 52 and 54 alongside each other in the lumen. Guidewire 12 is typically threaded through guide tube 22 such that following the threading:

(a) guidewire 12 enters a lumen of guide tube 22 from a distal-end 32 opening of guide tube 22, (b) guidewire 12 passes out of the lumen of guide tube 22 through hole 40 of guide tube 22, (c) first stent 52 is constrained from distal motion past hole 40 of guide tube 22, due to guidewire 12 being disposed within hole 40, (d) guidewire 12 passes into the lumen of guide tube 22 through proximal end 29 of slit 28, and (e) first stent 52 is constrained from proximal motion past proximal end 29 of slit 28, due to guidewire 12 being disposed within slit 28.

Following threading of guidewire 12 through guide tube 22 as described hereinabove, apparatus 20 is advanced into a body of the subject, e.g., into the small intestine, and into lumen 4 of the common bile duct, as shown in FIG. 3A. As shown, first stent 52 is advanced distally over guide tube 22 and against guidewire 12 (i.e., an outer surface of first stent 52 is disposed against guidewire 12). Due to threading of guidewire 12 as described hereinabove, stent 52 is advanced distally in lumen 4 while it is constrained from distal motion past hole 40 of guide tube 22. Constrained motion of stent 52 (particularly due to guidewire 12 being disposed within hole 40) typically allows for stent 52 to be advanced to a desired deployment site within lumen 4 in a controlled manner (i.e., inhibiting uncontrolled distal motion of stent 52, thus allowing the physician to safely perform the implantation at the desired deployment site).

Additionally, due to guidewire 12 being disposed within slit 28, first stent 52 is constrained from proximal motion past proximal end 29 of slit 28, allowing the physician to advance stent 52 in a controlled manner Reference is now made to FIGS. 3B-H.

Figure 3B:
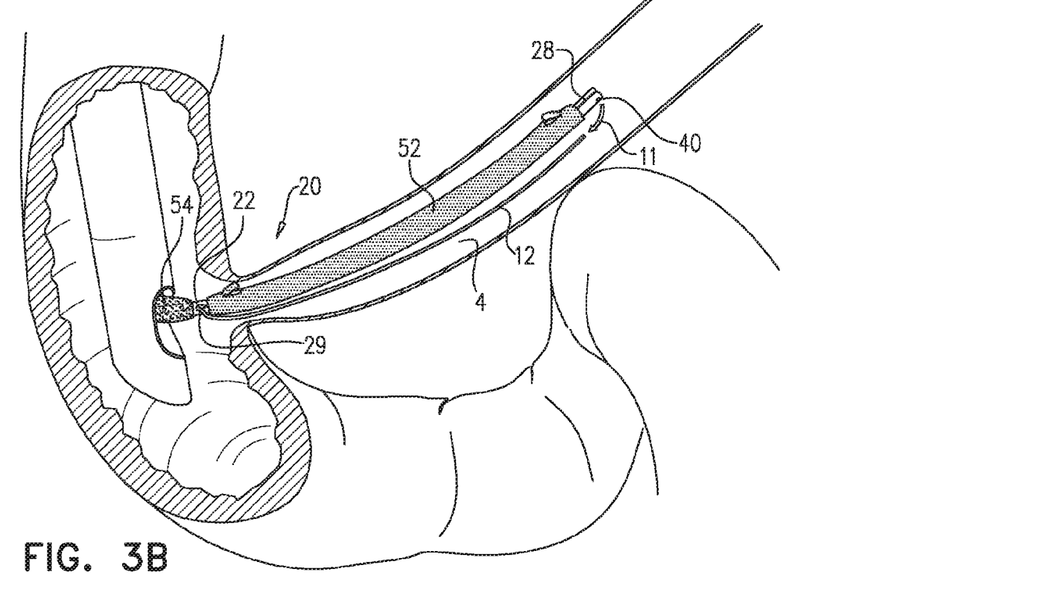
Figure 3C:
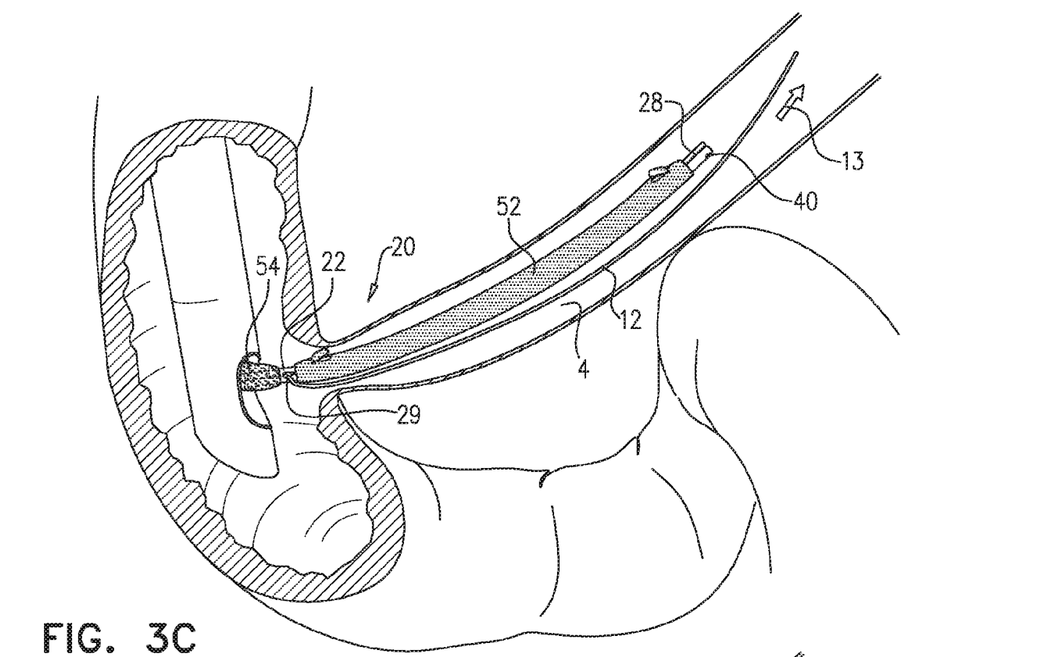
Figure 3D:
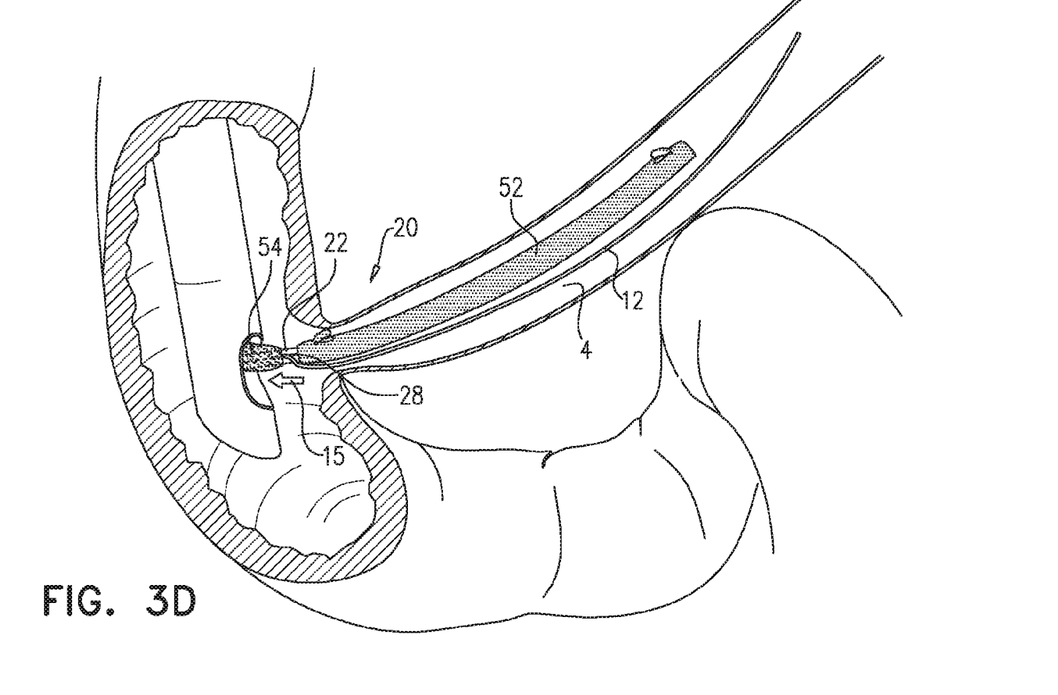
Figure 3E:
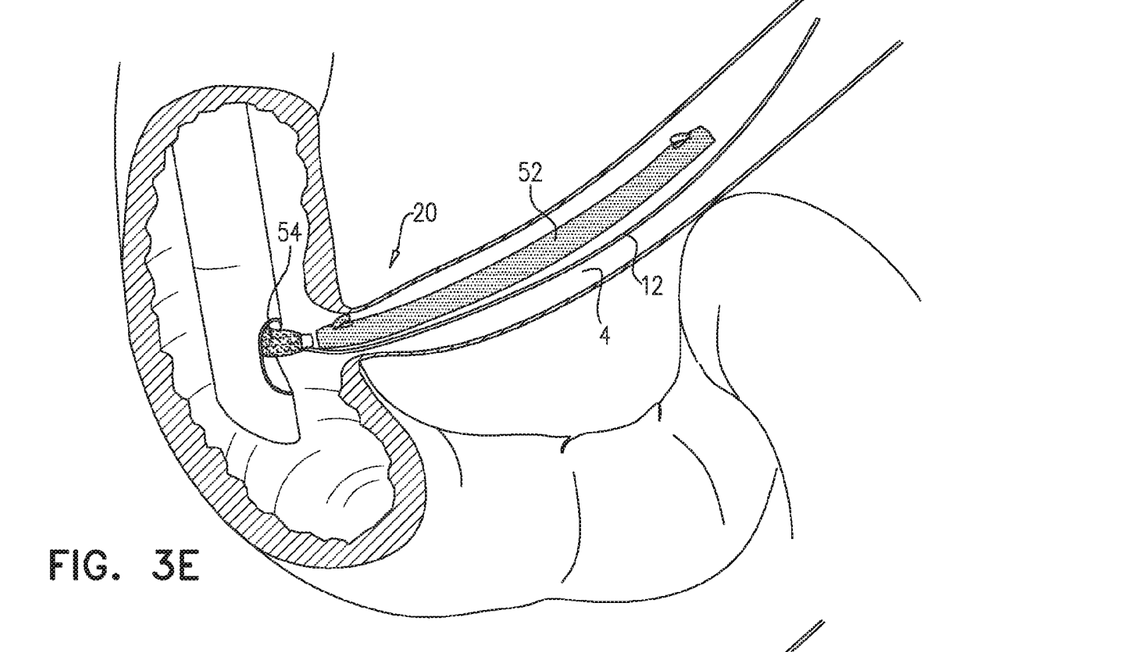

When first stent 52 reaches a desired deployment site within lumen 4, guidewire 12 is removed from hole 40 of guide tube 22, by pulling guidewire 12 proximally in the direction indicated by arrow 11, as shown in FIG. 3B. Guidewire 12 is then typically advanced distally in lumen 4 as indicated by arrow 13 (FIG. 3C). Guidewire 12 is thus maintained within lumen 4 and is not removed from lumen 4 at this stage. Removal of guidewire 12 from hole 40 typically releases first stent 52 and allows for guide tube 22 to be pulled proximally in the direction indicated by arrow 15 until guide tube 22 is removed from stent 52, and stent 52 can be deployed in lumen 4 (FIG. 3D). While pulling guide tube 22 proximally in the direction indicated by arrow 15, guidewire 12 slides through slit 28 of guide tube 22 and is consequently centered within a lumen of the guide tube (FIG. 3E). Centering of guidewire 12 in guide tube 22 facilitates using guidewire 12 for deployment of second stent 54 within lumen 4. Positioning of guidewire 12 in guide tube 22 using slit 28 allows second stent 54 to be advanced over guidewire 12, whereas first stent 52 was advanced against (but not while around) guidewire 12.

Figure 3F:
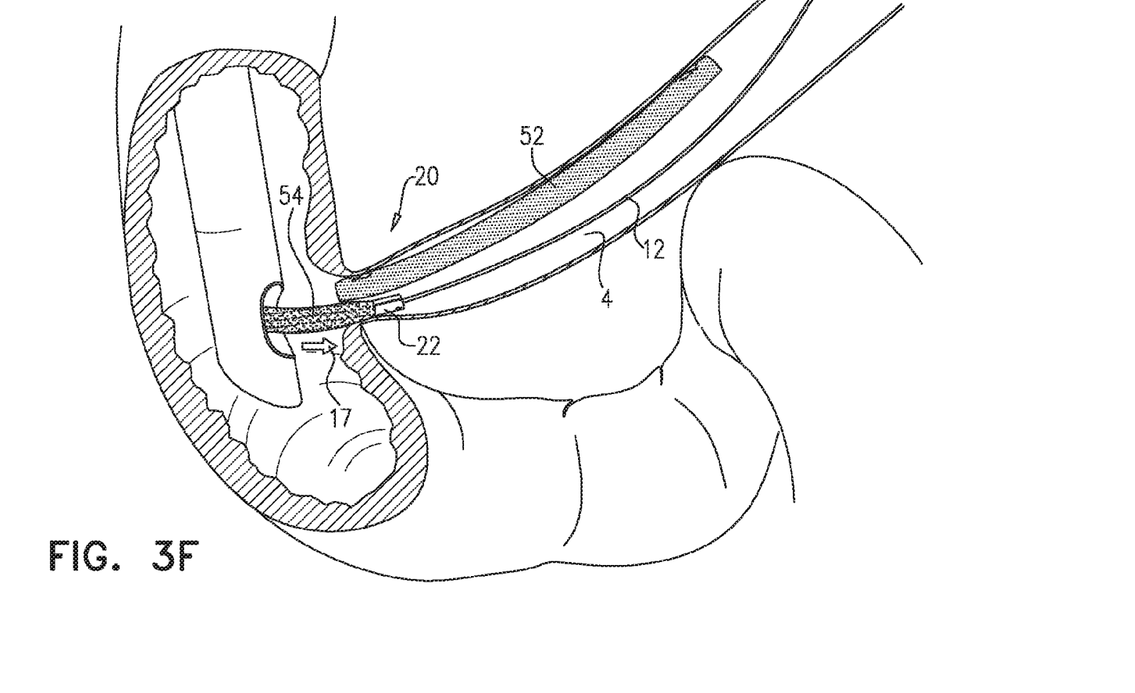
Figure 3G:
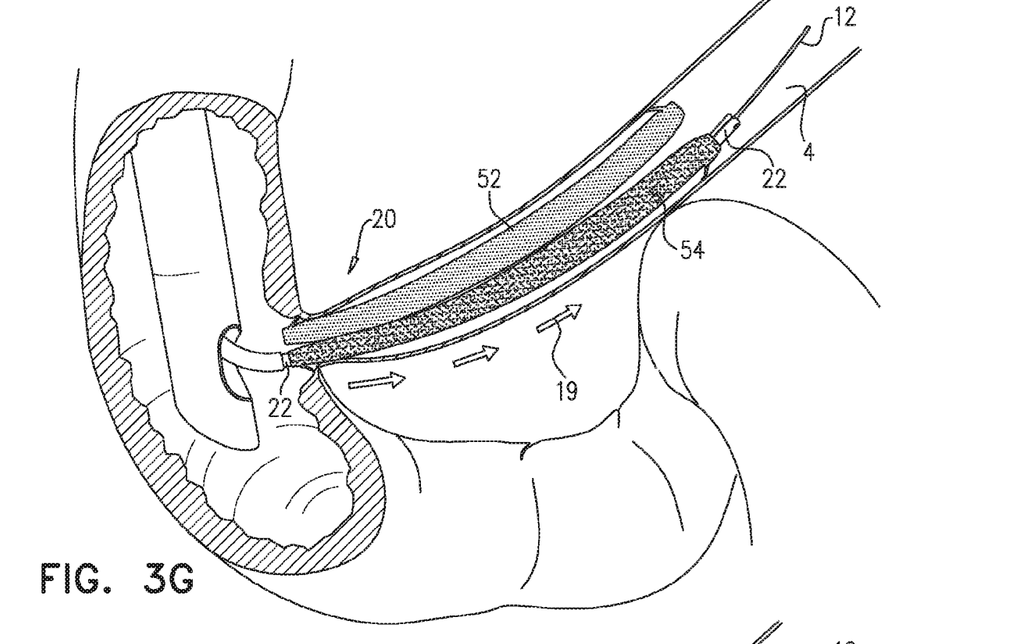

As shown in FIG. 3F, and indicted by arrow 17, second stent 54 is advanced distally in lumen 4 over guide tube 22 and over guidewire 12 (which is the lumen of guide tube 22). As shown in FIG. 3G, second stent 54 continues to be distally advanced in lumen 4 (as indicted by arrows 19) until a desired deployment site is reached alongside first stent 52 (FIGS. 3F-G). Once second stent 54 is deployed alongside first stent 52, guide tube 22 and guidewire 12 are retracted by being pulled in a proximal direction, as indicated by arrow 21 in FIG. 3H.

Figure 3H:
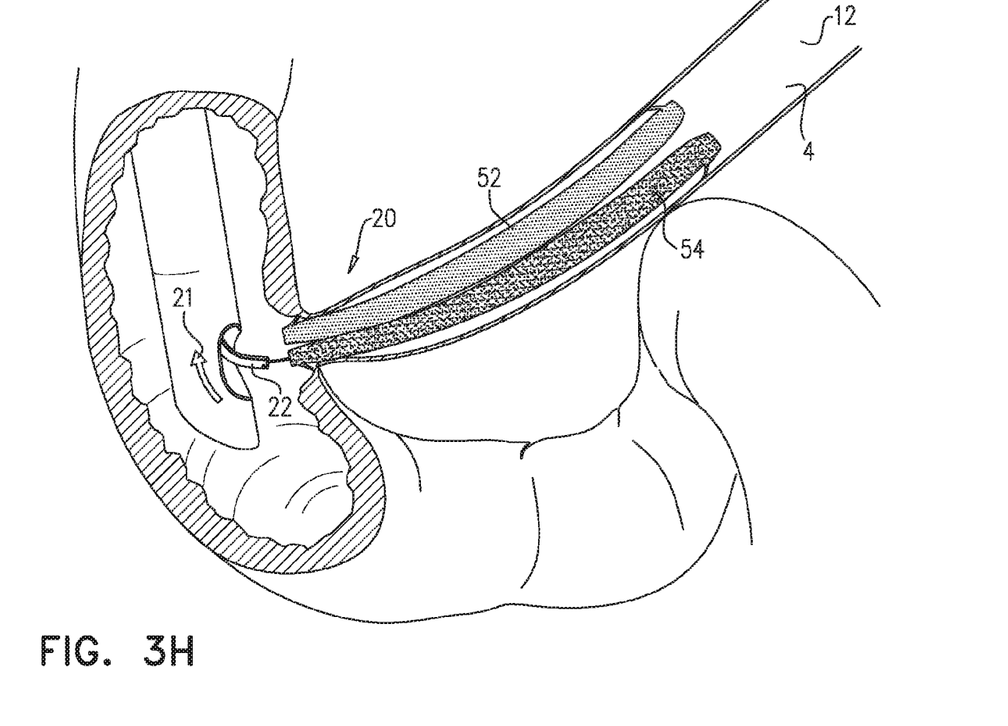

As described in FIGS. 3A-H, use of apparatus 20 in accordance with some applications of the present inventions, allows for deployment of second stent 54 subsequently to deployment of first stent 52, while maintaining guidewire 12 within lumen 4. Additionally, apparatus 20 allows for deployment of second stent 54 subsequently to deployment of first stent 52, without removing apparatus 20 from the body of the subject following deployment of first stent 52 in order to mount second stent 54. Notably, first and second stents 52 and 54 are typically disposed at the same time on guide tube 22 (also as shown in FIG. 2) when advanced into the subject's body, to be deployed within the lumen using the techniques described herein. Reference is made to FIGS. 2-3H. It is noted that for some applications first and second stents 52 and 54 comprise self-expandable stents.

It is additionally noted that stents are described by way of illustration and not limitation. The scope of the present invention includes the use of any other drainage tube or tube-like structure configured to relieve stricture of a lumen of a subject.

Figure 4:
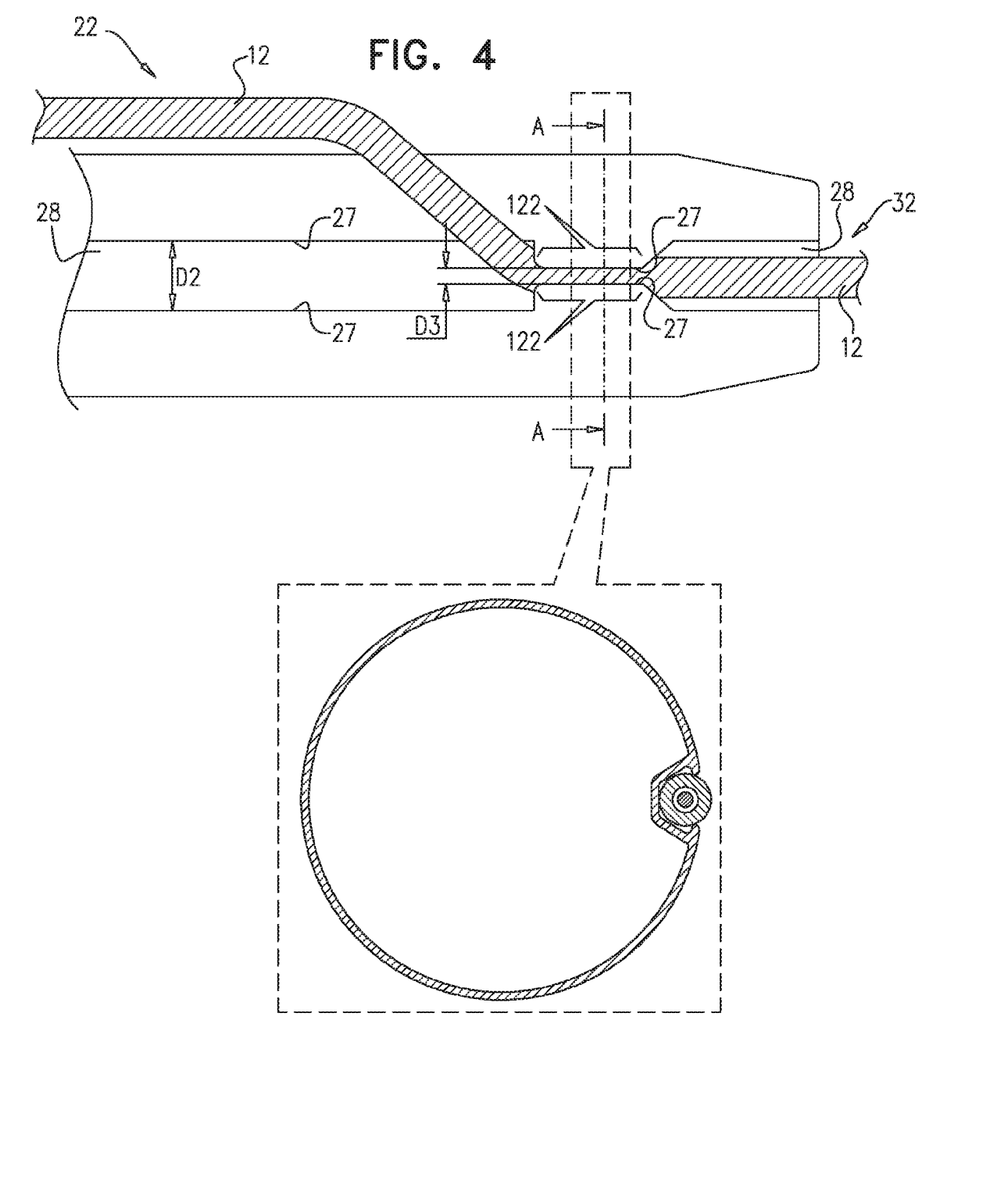
FIG. 4 is a schematic illustration of an additional configuration of the guide tube for deployment of the first and second stents in the lumen of the subject, in accordance with some applications of the present invention.

Reference is now made to FIGS. 3A-4. FIG. 4 is a schematic illustration of an additional configuration of guide tube 22 for deployment of first and second stents 52 and 54 in the lumen of the subject, in accordance with some applications of the present invention. As described hereinabove with reference to FIGS. 1-3H, guidewire-engaging portion 122, embodied as hole 40, is configured to engage guidewire 12 in such a way that it inhibits distal motion of first stent 52 past guidewire-engaging portion 122 of guide tube 22, due to guidewire 12 being engaged by portion 122 (e.g., disposed within hole 40). Guidewire-engaging portion 122 is shown in FIGS. 1-3H as hole 40 by way of illustration and not limitation. It is noted that guidewire-engaging portion 122 may be shaped to define any other configuration suitable for engaging guidewire 12 in such a manner that will grasp or otherwise hold guidewire 12 and thereby inhibit distal motion of first stent 52 past guidewire-engaging portion 122 when stent 52 is advanced distally against guidewire 12. It is noted that the techniques described herein with reference to FIGS. 3A-H apply to guidewire-engaging portion 122 as shown in FIG. 4 as well.

As shown in FIG. 4, for some applications, edges 27 of slit 28 are shaped to define guidewire-engaging portion 122. Typically, distance D2 between a first one of the slit edges and a second one of the slit edges is 0.45-0.9 mm. However, at guidewire-engaging portion 122, a distance D3 between slit edges 27 is smaller than distance D2, such that, for example, D2 is 2-5 times larger than D3. Typically, distance D3 between slit edges 27 is 0.09 mm-0.45 mm, e.g., greater than 0.15 mm and/or less than 0.4 mm. Typically, guidewire-engaging portion 122 shown in FIG. 4 has a length that is 5-10 times longer than D3, e.g., 0.45 mm-4.5 mm, e.g., greater than 1 mm and/or less than 3.5 mm. As shown in FIG. 4, guidewire 12 is typically engaged by, and locked into, the narrowed area in slit 28 which defines guidewire-engaging portion 122. Engaging guidewire 12 by guidewire-engaging portion 122 typically allows for first stent 52 to be advanced to a desired deployment site within the lumen of the subject in a controlled manner (i.e., inhibiting uncontrolled distal motion of stent 52 when stent 52 is advanced distally against guidewire 12, thus allowing the physician to safely perform the implantation at the desired deployment site).

In other words, when guidewire 12 is disposed (i) at least in part in a lumen of guide tube 22, (ii) passing through an opening at distal end 32 of guide tube 22, (iii) passing through guidewire-engaging portion 122 of guide tube 22, and (iv) passing through proximal end 29 of slit 28, first stent 52 is (i) constrained from distal motion past guidewire-engaging portion 122, and (ii) constrained from proximal motion past proximal end 29 of the slit 28. Additionally, when guidewire 12 is disposed (i) at least in part in a lumen of guide tube 22, (ii) passing through an opening at distal end 32 of guide tube 22, (iii) passing through guidewire-engaging portion 122 of guide tube 22, and (iv) passing through proximal end 29 of slit 28, second stent 54 is constrained from distal motion past the proximal end of the slit.

Once first stent 52 is in a desired deployment site in the lumen of the subject, guidewire 12 is released from guidewire-engaging portion 122 by pulling guidewire 12. Removal of guidewire 12 from guidewire-engaging portion 122 typically releases first stent 52 and allows guide tube 22 to be pulled proximally in the direction indicated by arrow 15 (as shown in FIG. 3D) until guide tube 22 is removed from stent 52, and stent 52 can be deployed in the lumen of the subject.

It is noted that for other applications, guidewire-engaging portion 122 may comprise a clip or any other suitable apparatus for engagement of guidewire 12.

Reference is made to FIGS. 1-4. It is noted that for some applications apparatus 20 is configured to deploy more than two stents, e.g., three or four stents, in the lumen of the subject (configuration not shown). Typically for such applications, guide tube 22 is shaped to define a second guidewire-engaging portion e.g., a second hole 40, on proximal portion 24 of tube 22.

Reference is still made to FIGS. 1-4. It is noted that apparatus 20 is described with reference to lumen 4 of a common bile duct by way of illustration and not limitation. The scope of the present invention includes use of apparatus 20 in any suitable lumen to deploy multiple stents in the lumen. For example, techniques and apparatus described herein may be used in a urethra, and/or in a ureter, and/or in a pancreatic duct, and/or in an esophagus, and/or in a trachea of the subject. Additionally or alternatively, techniques and apparatus described herein may be used to deploy two or more prostatic stents.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   using an apparatus including:
      a guide tube shaped to define (a) a guidewire-engaging portion at a distal portion of the guide tube, and (b) a continuous and open slit extending proximally along a wall of the guide tube, from a distal end of the guide tube, a proximal end of the slit being located distally to a proximal end of the guide tube,
      a first stent surrounding the guide tube, and
      a second stent, proximal to the first stent, surrounding a proximal portion of the guide tube; and
   threading a guidewire through the guide tube, such that, following the threading:
      (a) the guidewire-enters a lumen of the guide tube from a distal-end opening of the guide tube,
      (b) the guidewire passes through the guidewire-engaging portion of the guide tube,
      (c) the first stent is constrained from distal motion past the guidewire-engaging portion of the guide tube, due to the guidewire passing through the guidewire-engaging portion,
      (d) the guidewire passes through the proximal end of the slit and into the lumen of the guide tube, and
      (e) the first stent is constrained from proximal motion past the proximal end of the slit, due to the presence of the guidewire at the proximal end of the slit.

2. The method according to claim 1, further comprising:
   removing the guidewire from the guidewire-engaging portion;
   subsequently to the removing, advancing the first stent along the guide tube and off of the distal end of the guide tube;
   subsequently to advancing the first stent off of the distal end of the guide tube, advancing the second stent along the guide tube and surrounding the guidewire; and
   subsequently to advancing the first stent, advancing the second stent off of the distal end of the guide tube, and placing the second stent alongside the first stent.

3. Apparatus comprising:
   a guidewire;
   a first stent (i) having an outer surface disposed against the guidewire and (ii) configured to be advanced into a lumen of a subject while the outer surface is disposed against the guidewire;
   a second stent proximal to the first stent, surrounding the guidewire, and configured to be advanced into the lumen of the subject surrounding the guidewire; and
   a guide tube disposed within the first and second stents, the guide tube shaped to define a continuous and open slit extending proximally along a wall of the guide tube, from a distal end of the guide tube, a proximal end of the slit being located distally to a proximal end of the guide tube.

4. The apparatus according to claim 3, wherein the guide tube is further shaped to define a hole through the wall of the guide tube, the hole sized to allow the guidewire to pass therethrough into a lumen of the guide tube, and wherein the guide wire is disposed within the hole.

5. Apparatus for use with a guidewire, the apparatus comprising:
   a guide tube shaped to define (a) a guidewire-engaging portion at a distal portion of the guide tube, and (b) a continuous and open slit extending proximally along the wall of the guide tube, from a distal end of the guide tube, a proximal end of the slit being located distally to a proximal end of the guide tube;
   a first stent surrounding the guide tube so as to be advanceable together with the guide tube into a lumen of a subject, the first stent being slidable along the guide tube such that a proximal end of the first stent is disposed distally to the proximal end of the slit while a distal end of the first stent is disposed proximally to the guidewire-engaging portion, the first stent being slidably advanceable off the distal end of the guide tube; and
   a second stent, proximal to the first stent, surrounding a proximal portion of the guide tube, and shaped and sized to be advanceable along the guide tube and off the distal end of the guide tube into the lumen, and placed alongside the first stent subsequent to advancement of the first stent off the distal end of the guide tube.

6. The apparatus according to claim 5, wherein the guidewire-engaging portion comprises a hole disposed at the distal portion of the guide tube.

7. The apparatus according to claim 5, wherein when the guidewire is disposed (i) at least in part in the lumen of the guide tube, (ii) passing through a distal-end opening of the guide tube, (iii) passing through the guidewire-engaging portion of the guide tube, and (iv) passing through the proximal end of the slit, the second stent is constrained from distal motion past the proximal end of the slit.

8. The apparatus according to claim 5, further comprising the guidewire, wherein the guidewire is disposed (i) at least in part in the lumen of the guide tube, (ii) passing through a distal-end opening of the guide tube, (iii) passing through the guidewire-engaging portion of the guide tube, and (iv) passing through the proximal end of the slit, the first stent is (A) constrained from distal motion past the hole and (B) constrained from proximal motion past the proximal end of the slit due to the presence of the guidewire at the proximal end of the slit.

9. The apparatus according to claim 5, wherein the first stent is slidably advanceable off the distal end of the guide tube when the guidewire is not passing through the guidewire-engaging portion of the guide tube.

10. The apparatus according to claim 5, wherein the slit has a length that is: (a) greater than a length of the first stent, and (b) less than a sum of the length of the first stent and a length of the second stent.

11. The apparatus according to claim 5, wherein a distal end of the second stent is disposed proximally to the proximal end of the slit.

12. The apparatus according to claim 5, wherein the slit (i) defines two slit edges that are parallel to a central longitudinal axis of the guide tube and (ii) is shaped to define the guidewire-engaging portion and wherein a distance between a first one of the slit edges and a second one of the slit edges at the guidewire-engaging portion is smaller than a distance between the first one of the slit edges and the second one of the slit edges not at the guidewire-engaging portion.

13. The apparatus according to claim 12, wherein the distance between the first one of the slit edges and the second one of the slit edges at the guidewire-engaging portion is less than 0.4 mm.

14. The apparatus according to claim 12, wherein the distance between the first one of the slit edges and the second one of the slit edges not at the guidewire-engaging portion is 2-5 times greater than the distance between the first one of the slit edges and the second one of the slit edges at the guidewire-engaging portion.

15. The apparatus of claim 5, further comprising the guidewire, wherein the first and second stents are pre-loaded on the guide tube such that (i) the first stent surrounds the guide tube at a given time and (ii) the second stent is proximal to the first stent and surrounds a proximal portion of the guide tube at the same given time.

* * * * *